United States Patent [19]  
Bolzan et al.

[11] Patent Number: 4,678,612  
[45] Date of Patent: Jul. 7, 1987

[54] PROCESS FOR THE PRODUCTION OF ARYLSULFONYL HALIDES

[75] Inventors: Louis F. Bolzan, Briarcliff Manor; Edward D. Weil, Hastings-on-Hudson, both of N.Y.

[73] Assignee: Stauffer Chemical Company, Westport, Conn.

[21] Appl. No.: 824,741

[22] Filed: Jan. 31, 1986

[51] Int. Cl.$^4$ ............................................. C07C 143/70
[52] U.S. Cl. .................................................. 260/543 R
[58] Field of Search .................................... 260/543 R

[56] References Cited

U.S. PATENT DOCUMENTS

| | | | |
|---|---|---|---|
| 3,644,515 | 2/1972 | Suzuki | 260/543 R |
| 3,795,705 | 3/1974 | Chan | 260/543 R |
| 3,845,194 | 10/1974 | Somlo et al. | 260/543 R |
| 4,105,692 | 8/1978 | Blank | 260/543 R |

OTHER PUBLICATIONS

*Derwent Abstract* 44,761 D25 *J6 6046-860 (JP 123,124 issued Apr. 28, 1981).

*Primary Examiner*—Natalie Trousof  
*Assistant Examiner*—L. Hendriksen  
*Attorney, Agent, or Firm*—Hensley M. Flash

[57] ABSTRACT

There is disclosed a process for the production of arylsulfonyl halides, e.g., benzenesulfonyl chloride. The disclosed process adds a phosphorus-containing additive, e.g., phosphorous acid, before the reaction of an arylsulfonic acid with a sulfur halide and a halogen. The phosphorus-containing additive reduces the thermal instability of the residue remaining after distillation of the arylsulfonyl halide.

10 Claims, 2 Drawing Figures

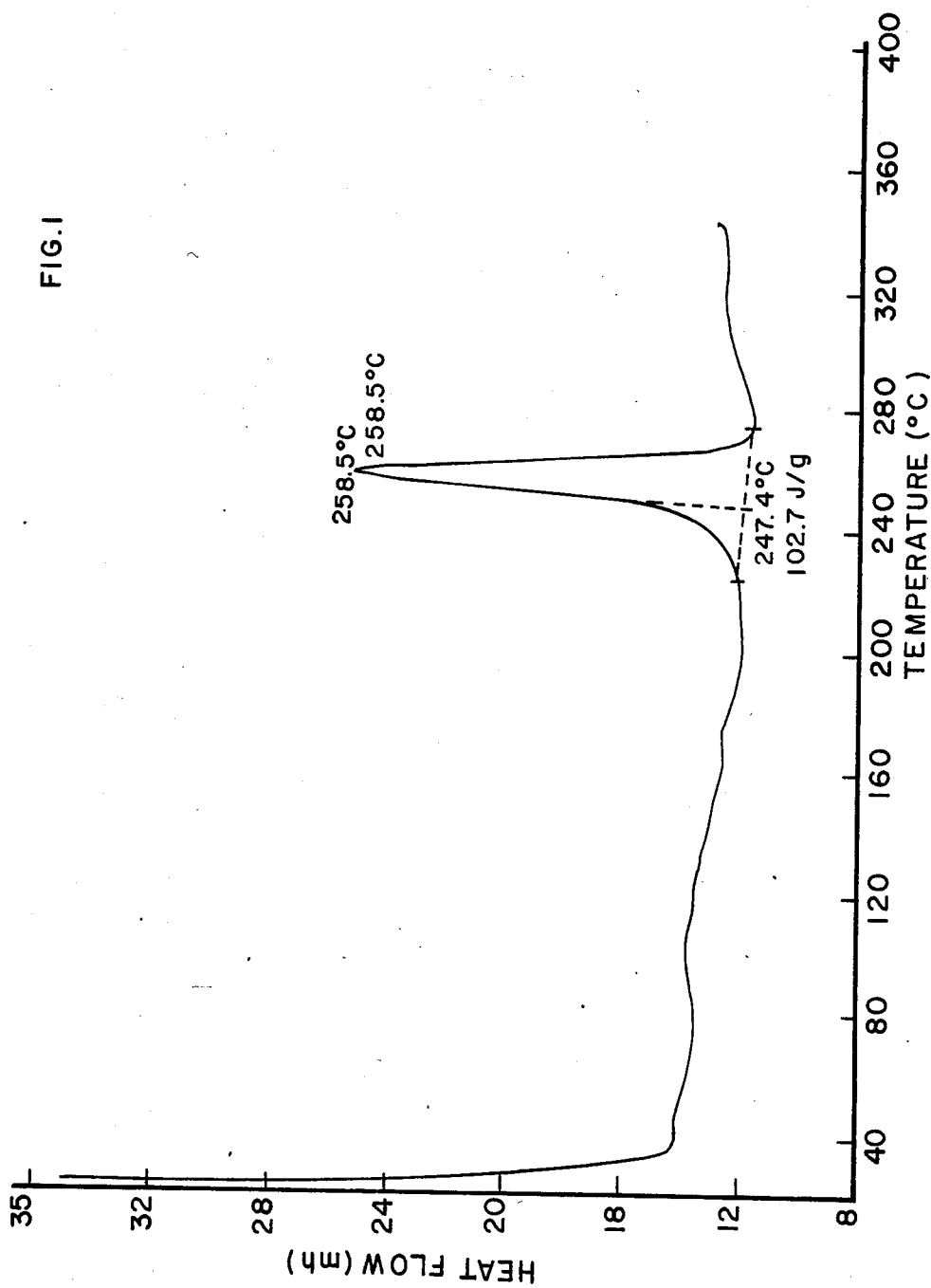

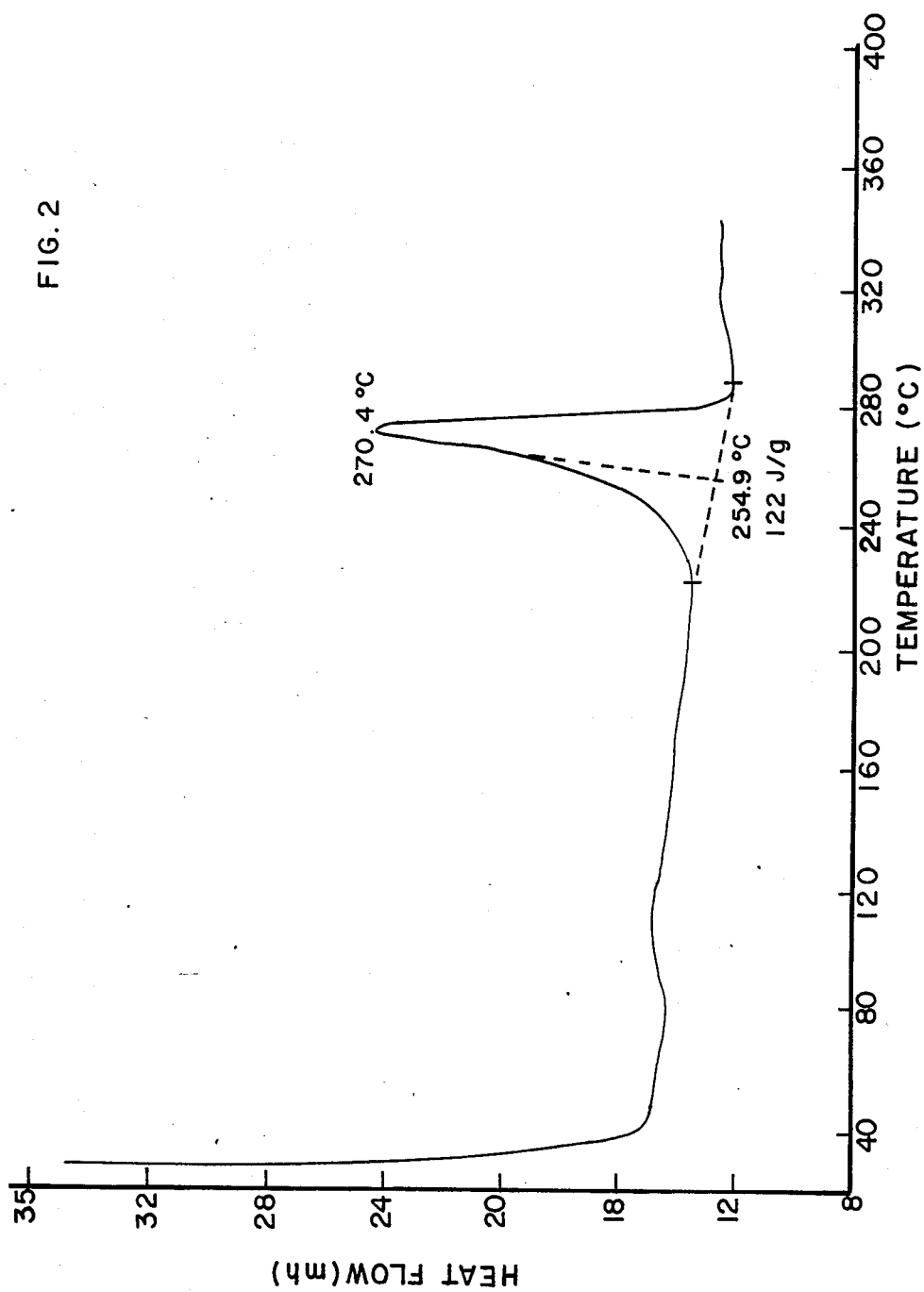

PROCESS FOR THE PRODUCTION OF ARYLSULFONYL HALIDES

FIELD OF THE INVENTION

The present invention relates to an improved process for the production of arylsulfonyl halides, and more particularly to a process wherein the decomposition of the residue resulting after distillation is inhibited.

BACKGROUND OF THE INVENTION

Arylsulfonyl halides, such as, for example, benzenesulfonyl chloride, are particularly useful as intermediates in the manufacture of certain biologically active compounds. For example, benzenesulfonyl chlorides can be reacted with primary or secondary amines to produce certain arylsulfonamides such as, for example, N-(beta-O,O-diisopropyldithiophosphorylethyl)benzenesulfonamide.

These arylsulfonyl halides may be produced by any number of methods. For instance, the most commonly employed procedure is the reaction of an arylsulfonic acid with either thionyl chloride or phosphorus pentachloride. Other methods include the reaction of an arylsulfonic acid with thionyl chloride in the presence of a sulfonating agent (U.S. Pat. No. 4,105,692), and the reaction of an arylsulfonic acid with a carbonyl halide in the presence of dimethylformamide and a tertiary amine (U.S. Pat. No. 3,795,705). Another method reacts an arylsulfonic acid with a sulfur monohalide in the presence of excess halogen. The latter method is especially useful in the production of benzenesulfonyl chloride wherein benzenesulfonic acid, sulfur monochloride and chlorine are reacted to produce benzenesulfonyl chloride.

In the processes discussed above, the arylsulfonyl halide produced can be removed by distillation. However, because of the heterogeneous nature of the reaction mixture, the residue which remains after distillation decomposes at such a rapid rate that a safety hazard is presented. Thus, it would be advantageous from both an economic standpoint and a safety viewpoint to inhibit the decomposition of this residue.

SUMMARY OF THE INVENTION

In accordance with the present invention, there is disclosed a process for the production of arylsulfonyl halides. The disclosed process comprises (a) adding to an arylsulfonic acid an effective amount of a phosphorus-containing additive, said additive capable of yielding phosphoric acid under conditions of oxidation or hydrolysis, (b) reacting the arylsulfonic acid/phosphorus-containing additive mixture of (a) with a sulfur halide and a halogen. In this process the phosphorus-containing additive is selected from the group consisting of phosphorous acid, phosphoric acid, phosphorus trichloride, phosphorus oxychloride, esters of phosphorous acid and esters of phosphoric acid.

IN THE DRAWINGS

FIG. 1 is a Differential Scanning Calorimetry (DSC) graph of the thermal decomposition of the residue remaining after distilling off benzenesulfonyl chloride (BSC).

FIG. 2 is a Differential Scanning Calorimetry (DSC) graph of the thermal decomposition of the residue remaining after distillation of BSC with the addition of PCl$_3$ before addition of the halogenating agent.

DETAILED DESCRIPTION OF THE INVENTION

The present invention is directed to a process for inhibiting decomposition in the distillation of arylsulfonyl halides. These arylsulfonyl halides are derived from an arylsulfonic acid of the general formula:

ArSO$_3$H wherein Ar represents an aryl moiety which includes phenyl or substituted phenyl, naphthyl or substituted naphthyl and heteroacylic aromatic compounds. The substituents include halides and particularly chlorine, bromine, fluorine, iodine, alkyl and alkenyl groups, preferably lower alkyl or lower alkenyl, aryl, nitro, cyano, alkoxy, carboalkoxy, acyloxy, acylamido, acyl, formyl, alkyl mercapto, aryl mercapto, alkylsulfinyl, arylsulfinyl, alkylsulfonyl, arylsulfonyl and alkenylsulfonyl.

The arylsulfonic acid used in the present invention can also be in the form of a metal salt represented by the formula:

ArSO$_3$M wherein Ar is as defined above, and M represents an alkali or alkaline earth metal, which for reasons of cost and availability, will preferably be sodium or potassium. As used in regard to the present invention, the term "arylsulfonic acid" shall be inclusive of both the acid and salt forms thereof.

Illustrative of those sulfonic acids which can be used in the present invention, in either the form of an alkali or alkaline earth metal salt or in the free sulfonic acid form, are benzenesulfonic acid, chlorobenzenesulfonic acid, trichlorobenzenesulfonic acid, toluenesulfonic acid, 1-naphthalenesulfonic acid, 2-naphthalenesulfonic acid, 2-anthraquinonesulfonic acid, 4-pyridinesulfonic acid, 2-thiophenesulfonic acid, p-methoxybenzenesulfonic acid, p-carbomethoxybenzenesulfonic acid, p-acetoxybenzenesulfonic acid, p-acetylbenzenesulfonic acid, m-acetylbenzenesulfonic acid, o-acetylbenzenesulfonic acid, p-formylbenzenesulfonic acid, m-formylbenzenesulfonic acid, p-cyanobenzenesulfonic acid, p-acetylaminobenzenesulfonic acid, p-nitrobenzenesulfonic acid, p-methylmercaptobenzenesulfonic acid, p-phenylmercaptobenzenesulfonic acid, p-phenylsulfonylbenzenesulfonic acid and the like.

To produce the arylsulfonyl halide, the arylsulfonic acid described above is reacted with a halogen-supplying reagent which can be represented by any of the formulas:

SOX$_2$, SO$_2$X$_2$, PX$_3$, PX$_5$, POX$_3$, C(O)(X)$_2$, SX$_2$ or S$_2$X$_2$ wherein X is a halogen.

Exemplary halogen-supplying reagents represented by the above formulas can include thionyl chloride, sulfuryl chloride, phosphorus trichloride, phosphorus pentachloride, phosphorus oxychloride, sulfur dichloride and sulfur monochloride as well as the bromine analogues thereof. In a preferred embodiment of the present invention, the arylsulfonic acid is halogenated using a sulfur halide in the presence of halogen. The remaining description of the invention will be discussed in relation to the reaction of an arylsulfonic acid with a sulfur halide and halogen to produce an arylsulfonyl halide although it is to be understood that the present discussion applies equally to an arylsulfonyl halide produced by any of the previously discussed methods.

In a preferred embodiment of the present invention, an arylsulfonic acid is reacted with a sulfur monohalide in the presence of halogen to produce the desired arylsulfonyl halide. This reaction can be expressed as follows:

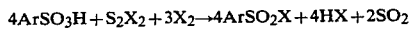

$$4ArSO_3H + S_2X_2 + 3X_2 \rightarrow 4ArSO_2X + 4HX + 2SO_2$$

The above reaction can also be treated as a series of separate reactions. In one series of reactions, the halogen reacts with sulfur or the sulfur halide, a reaction whose chemistry is described by the following reactions:

| (a) | $2S + X_2 \rightarrow S_2X_2$ | (i) |
| (b) | $S_2X_2 + X_2 \rightleftharpoons 2SX_2$ | (ii) |
| (c) | $SX_2 + X_2 \rightleftharpoons SX_4$ | (iii) |
| (d) | $2ArSO_3 + 2S_2X_2 \rightarrow 2ArSO_2X + 3S + HCl$ | |

The arylsulfonic acid can then react with either of species (i), (ii) or (iii) to produce the desired arylsulfonyl halide as exemplified by reaction (d). While any of the above reactions do result in the formation of the arylsulfonyl halide, they also result in the formation of a residue which decomposes rapidly and presents a safety hazard. The exact form of this residue is not known but it is believed that the residue can be various mixtures of arylsulfonyl halide derivatives exemplified by the following formula:

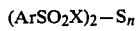

$$(ArSO_2X)_2-S_n$$

wherein Ar and X are as previously defined and n or m is an integer from 1 to 6.

While the exact nature of the decomposition reaction is not known, it is also believed that the rapid decomposition of this residue is catalyzed by iron or antimony impurities in the reaction mixture. Moreover, the residue reacts rapidly with sulfur halide to produce a metal halide, thereby reducing the yield of the desired product, arylsulfonyl halide. It has now surprisingly been found that the decomposition of the residue can be reduced, i.e., residue stability can be increased, by the addition of phosphorus compounds to the reaction mixture. It is believed that the phosphorus compounds act as chelating agents binding the iron and antimony impurities, thereby reducing the adverse effect of these impurities. However, this is only a theory and we do not wish to be bound thereby.

The phosphorus-containing compounds which can be used in the present invention are those which yield phosphoric acid under hydrolysis or oxidation conditions. These compounds can include phosphorous acid, phosphorus oxychloride, phosphorus trichloride, phosphorus, phosphorus pentasulfide, thiophosphorus trichloride, phosphorus oxytrichloride, phosphorus pentachloride, as well as organic esters of phosphoric and phosphorous acid. These compounds can be classified as phosphorus-containing additives yielding phosphoric acid under oxidation or hydrolysis conditions. Throughout this specification, the term "phosphorus-containing additive" refers to the above compounds.

Inorganic salts, especially alkali or alkaline earth metal salts of the above phosphorus-containing additives can also be used.

The phosphorus-containing additive is preferably added to the arylsulfonic acid before the halogenating agent is added. The amount of phosphorus-containing additive added to the reaction mixture is based on the arylsulfonic acid and can range from about 0.02 to about 2 weight percent.

The reaction temperature can range from about 60° C. to about 120° C. Once the reaction is complete, the desired product can be distilled without decomposition of the residue under normal distillation conditions. The stabilized residue can then be removed from the reaction mixture and properly disposed of.

The following Experiments describe various embodiments of the invention. Other embodiments will be apparent to one of ordinary skill in the art from a consideration of this specification or practice of the invention disclosed herein. It is intended that the specifications and Experiments be considered as exemplary only, with the true scope and spirit of the invention being indicated by the claims which follow the Experiments.

EXPERIMENT 1

This Experiment illustrates the overall process for the production of benzenesulfonyl chloride and the stabilization of the residue.

To a 1 liter flask was added 808 grams (5.1 mole) of benzenesulfonic acid and 5.7 grams of a 70 percent solution of phosphorous acid (4.0 grams phosphorous acid/1.7 grams water). Sulfur monochloride addition was started and after all the sulfur monochloride had been added, chlorine was bubbled into the reaction mixture for a period of 20 hours at 80° C. The resultant benzenesulfonyl chloride was removed by distillation.

COMPARATIVE EXPERIMENT 1

An experiment similar to Experiment 1 was carried out except that phosphorous acid was not added before the addition of sulfur monochloride. The results of Differential Scanning Calorimetry (DSC) of the thermal decomposition of the residue remaining after distillation is shown in FIG. 1.

EXPERIMENT 2

An experiment similar to Experiment 1 was carried out except that PCl$_3$ was added to inhibit the decomposition of the BSC. The DSC results are shown in FIG. 2.

In the DSC analyses discussed above and presented in FIGS. 1 and 2, the samples were heated at 20° C. per minute. The peaks in the curves occurred where decomposition of the residue generated heat.

In FIGS. 1 and 2, the peaks occurred at 258° C. and 270° C. respectively. This 12° C. difference is significant because the peak temperatures correlate with the length of time that the material being tested can be held at a constant temperature before decomposing. At 150° C., which is the final distillation temperature, the time to decomposition is usually increased from about 8 hours to about 45 hours when the process of the present invention is used. This longer time to decomposition allows satisfactory plant operations whereas the shorter time does not.

What is claimed is:

1. A process for the production of arylsulfonyl halides which comprises:
   (a) adding to an arylsulfonic acid an effective amount of a phosphorus-containing additive, said additive capable of yielding phosphoric acid under conditions of oxidation or hydrolysis,
   (b) reacting the arylsulfonic acid/phosphorus-containing additive mixture of (a) with a sulfur halide and a halogen.

2. The process of claim 1 wherein the phosphorus-containing additive is selected from the group consisting of phosphorous acid, phosphoric acid, phosphorus trichloride, phosphorus oxychloride, esters of phosphorous acid, and esters of phosphoric acid.

3. The process of claim 1 wherein the phosphorus-containing additive is phosphorous acid.

4. The process of claim 1 wherein the phosphorus-containing additive is phosphoric acid.

5. The process of claim 1 wherein the phosphorus-containing additive is phosphorus trichloride.

6. The process of claim 1 wherein the arylsulfonic acid is benzenesulfonic acid.

7. The process of claim 1 wherein the sulfur halide is sulfur monochloride.

8. The process of claim 1 wherein the halogen is chlorine.

9. The process of claim 1 wherein the arylsulfonyl halide produced is benzenesulfonyl chloride.

10. The process of claim 8 wherein the phosphorus-containing additive is phosphorous acid, the arylsulfonic acid is benzenesulfonic acid, and the sulfur halide is sulfur monochloride.

* * * * *